(12) United States Patent
Ben-Asouli et al.

(10) Patent No.: US 7,074,313 B2
(45) Date of Patent: Jul. 11, 2006

(54) PROCESSING CHAMBER

(75) Inventors: Yitzhak Ben-Asouli, Kfar Hanagid (IL); Farhat Osman, Sachnin (IL)

(73) Assignee: Gene Bio-Application Ltd., Kfar Hanagid (IL)

( * ) Notice: Subject to any disclaimer, the term of this patent is extended or adjusted under 35 U.S.C. 154(b) by 485 days.

(21) Appl. No.: 10/302,768

(22) Filed: Nov. 22, 2002

(65) Prior Publication Data
US 2003/0133846 A1    Jul. 17, 2003

Related U.S. Application Data

(63) Continuation of application No. PCT/IL01/00465, filed on May 22, 2001.

(30) Foreign Application Priority Data
May 25, 2000    (IL) ..................................... 136379

(51) Int. Cl.
*G01N 27/453*    (2006.01)
*B01D 35/06*    (2006.01)

(52) U.S. Cl. ..................... 204/613; 204/627; 204/639; 204/646; 73/863.23

(58) Field of Classification Search ............... 204/613, 204/627, 636, 638, 639, 640; 210/321.6, 210/321.71; 73/863.21–863.23, 864.81, 73/864.83

See application file for complete search history.

(56) References Cited

U.S. PATENT DOCUMENTS 4,545,888 A    10/1985 Walsh
4,576,702 A    3/1986 Peck et al.

(Continued)

FOREIGN PATENT DOCUMENTS

DE    94 17 714.7    2/1995

(Continued)

OTHER PUBLICATIONS

Definition of cylinder in Webster's Ii: New Riverside University Dictionary, the Riverside Publishing Company (Houghton Mifflin Company), 1994.*

*Primary Examiner*—Alex Noguerola
(74) *Attorney, Agent, or Firm*—Martin Fleit; Paul D. Bianco; Fleit Kain Gibbons Gutman Bongini & Bianco, P.L.

(57) ABSTRACT

A device having a processing chamber, for electroelution and/or dialysis of a substance carried in a sample with respect to an external liquid medium. The chamber has a closed end and an opening at the other end, sufficiently large to permit a sample, particularly a gel contained sample, to be inserted thereto. The chamber has two portals, each laterally disposed with respect to the opening. A tubular membrane covers the portals, and is sealingly fixed onto an outside surface of the housing. The device provides high yield recovery, saves time and allows for easy handling, especially regarding loading an unloading of small volume samples for dialysis, or inserting the gel slice containing the macromolecule sample. The device may be partially immersed in the liquid medium, with the opening above the liquid surface. Optionally, the device may be hermetically sealed via a cap, and fully immersed in the liquid medium.

44 Claims, 7 Drawing Sheets

U.S. PATENT DOCUMENTS

| | | |
|---|---|---|
| 4,608,147 A | 8/1986 | Clad |
| 4,685,813 A | 8/1987 | Moog |
| 4,699,706 A | 10/1987 | Burd et al. |
| 4,711,365 A * | 12/1987 | Fomby .................. 220/288 |
| 4,809,871 A * | 3/1989 | Angelchik .................. 220/789 |
| 4,964,961 A | 10/1990 | Brautigam et al. |
| 5,102,518 A | 4/1992 | Doering et al. |
| 5,109,997 A * | 5/1992 | Phillips .................. 215/360 |
| 5,200,073 A | 4/1993 | Steere et al. |
| 5,503,741 A | 4/1996 | Clark |
| 5,538,614 A * | 7/1996 | Han .................. 204/613 |
| 5,552,640 A | 9/1996 | Sutton et al. |

FOREIGN PATENT DOCUMENTS

| | | |
|---|---|---|
| GB | 239777 | 9/1925 |
| WO | WO 94/01763 | 1/1994 |
| WO | WO 96/26291 | 8/1996 |
| WO | WO 98/26859 | 6/1998 |
| WO | WO 99/02959 | 6/1998 |

* cited by examiner

Section D-D

PROCESSING CHAMBER

RELATED APPLICATION

This application is a continuation of International Application PCT/IL01/00465 filed May 22, 2001 designating the United States of America, for which priority is claimed under 35 USC 120

BACKGROUND OF THE INVENTION

1. Field of the Invention

The present invention relates to a device and method for electroelution and also for dialysis, in particular such a device that is disposable. This invention more specifically relates to a device and method for the isolation of macromolecules, including proteins and nucleic acids, from a gel to a suitable solution within the device and for optionally further dialysing such macromolecules while still in the same device.

2. Background (Prior Art)

Agarose or polyacrylamide gel electrophoresis has been an essential and very powerful method for the purification or analyzing of proteins and nucleic acids in micro scale biochemical studies. Running macromolecules in such gel matrices plays a major role in molecular biology. The composition of the gel matrices may be chosen such as to enable separation of almost any macromolecule from a large pool comprising many different macromolecules allowing to serve as a tool for separate one molecule of interest. Depending upon various physical/chemical characteristics, a sample comprising different-sized macromolecules migrates through the electrical field at a particular velocity. After electrophoresis, the gel is removed from the electrophoresis chamber, if needed, stained with reagents specific for proteins and/or nucleic acids, destained with organic solvent mixtures and photographed. Whereas electrophoretic separation of macromolecules is an established technique, the elution of macromolecules from the gel has hitherto represented a difficult and generally non-reproducible procedure. Harvesting such macromolecules is potentially of commercial value because of their applications in science and medicine. The major problem is at recovering or extracting those macromolecules in high yields for down stream protocols. Examples of such down stream protocols include:- (a) Using a DNA fragment extracted from an agarose or polyacrylamide gel for constructing a new plasmide; (b) Separating a target macromolecule from contaminant molecules, for example double strand RNA (dsRNA) from single strand RNA, for using the dsRNA in activation of PKR; (c) Extraction of a protein from a polyacrylamide gel for use as antigen in vaccination; (d) Extraction of DNA or proteins for sequencing. In particular, recovery or extraction of macromolecules from agarose or polyacrylamide in high yields is a major problem. This problem becomes more severe as the size of the molecule of interest is increased or the percentage concentration of the gel of the separating matrix is high. Over the last decade or so, various attempts have been made to improve the yields of the recovering of macromolecules from gels.

Perhaps the simplest procedure for the elution of macromolecules involves a dialysis membrane. In one method, the membrane is in the form of a tubular skin that is closed at both ends after inserting the gel containing the sample. While the method represents an improvement in yield, it requires special skill to handle the sample, as well as to tie or clamp one end of the tube to form a sack and then the other end. Furthermore leakage and the presence of air bubbles interfere with the electric field.

Many research laboratory use an elution protocol to recover DNA or RNA from polyacrylamide gels which is a time consuming protocol with two major drawbacks, low yields (10–20% depend on the size of the eluted molecule) and sensitivity of the molecules to low contamination like DNase, RNase or Protases in the elution solution.

A similar approach has been taken to elute nucleic acids from agarose gels. Here, agarose gel is melted by heating to 65° C. The mixture is extracted with phenol and the samples eluted. As expected, recoveries are usually low with this procedure. In addition, phenol is a highly toxic and biohazardous substance. Since diethylaminoethyl (DEAE) cellulose binds deoxyribonucleic acid (DNA), it has been employed to elute DNA from gels. The procedure involves i) electrophoretic transfer of DNA from gels to DEAE-paper. ii) alternatively, DEAE-paper is inserted into slots immediately under each band, thus DNA is transferred electrophoretically. Although these procedures yield excellent recoveries, they are highly dependent on technique and the apparatus is expensive.

Decomposing, the gel with chemicals, followed by trapping the macromolecules on glass beads and their elution with salt solution is another method of elution. However, this method is dependent on buffer conditions and the solution that in use for the digestion contains significant contamination material in it and needs to wash out. More than that, this method recovers specially DNA or RNA from agarose and not from polyacrylamide gel, and the method cannot be used for the extraction of proteins.

To solve some of the problems represented above, another method was developed, using a container comprising a rigid tubular member having open ends that are sealed with membranes after the slice of the gel containing the sample molecule is inserted. Again, skill is required by the user, and the method is generally difficult and cumbersome. Furthermore, the device is reusable, requiring pretreatment before each use, leading to potential contamination problems and/ or increasing complexity of use. Some new Electro-Eluter devices were developed that can process up to six samples simultaneously, but the devices represent high capital outlays. In many of those new Electro-Eluter devices, the sample is open to the environmental (ambient) air, which allows it to be easily contaminated. In order to reuse such devices, cleaning protocols need to be carefully followed to eliminate any contamination.

In 1985, Kartenbech introduced an electroelution apparatus (U.S. Pat. No. 4,552,640). This apparatus consists of an upper electrode in the upper chamber and the lower chamber to hold buffer solution and a lower electrode. The upper chamber is separated from the lower chamber by a septum, and the two chambers are connected by a connecting passage within the septum. The end of the lower chamber holds a dialysis membrane, wherein the electrophoretically eluted protein or polypeptide is collected. There are several disadvantages with this apparatus, including: i) since the volume of the lower chamber is large, it results in dilution of the sample, and ii) since the surface area of the dialysis membrane is large it results in non-specific adsorption of macromolecules resulting in very low recoveries.

In 1985, Walsh introduced an apparatus to elute nucleic acids (U.S. Pat. No. 4,545,888). This apparatus has features to introduce multiple copies of transfer chamber, filter discs to hold DEAE cellulose and negative electrode. Basically, in this procedure the sample is electrophoresed and collected on DEAE resin (held by a filter disc) at the bottom end of the lower chamber. Next, the filter disc is removed and DNA eluted from the resin employing standard elution protocols. This procedure requires an additional step involving the solution of nucleic acids from DEAE. Moreover, its application to elute proteins and polypeptides is uncertain.

In 1987, Burd introduced an electroelution method and apparatus (U.S. Pat. No. 4,699,706). This apparatus has features in which the electroeluted sample passes through a glass frit and is collected in a semipermeable membrane at the bottom end of the lower chamber. In this apparatus the dialysis membrane must be held in place by a retaining ring, a gasket and internal shoulders built in the equipment. There are several disadvantages with this equipment. For example, i) this is a rather complex setup and the success depends upon the technique used, ii) because the dialysis membrane is smaller then the diameter of the glass frit, it results in poor recovery, iii) use of dialysis membrane results in non-specific adsorption of macromolecules, which also contributes to low recovery, iv) there is no possibility of capping the columns to harvest the sample collected in the membrane, v) when the sample cup is removed, it leads to the disruption of the sample collected as it leaks through the filter disc and/or fluid held in the sleeve holding the cup.

In 1986, Clad introduced an apparatus for electroeluting macromolecules from gel (U.S. Pat. No. 4,608,147). This apparatus contains an upper chamber which holds a permeable membrane. (pore size about 0.2 micrometer) through which macromolecules can migrate downstream. The sample is collected in the lower chamber on top of an impermeable membrane having a molecular weight greater than 1000. Following elution, the polarity of the electric field is reversed for 10 to 15 seconds, so that the macromolecules adsorbed to the inner surface of the outer membrane are released from the membrane into the trap space. There are several disadvantages of this apparatus, including: i) the use of an impermeable membrane in the lower chamber results in dilution of sample, thus requiring further concentration, ii) because the sample is contaminated with the electrophoretic buffer, an additional step (e.g. dialysis) is required to remove such contaminants.

In 1990, Brautigam and Gorman introduced an electroelution apparatus (U.S. Pat. No. 4,964,961). This equipment consists of a tapered tube divided by a porous disc into an open upper section and a lower section which can be closed by a removable cap. The equipment has a dialysis membrane equal to the diameter of the removable cap and is affixed to it to close off the lower section. After electroelution, the upper section is closed. The sample is collected through the cup and dialysis membrane at the bottom end of the tube. Some disadvantages of this equipment include: i) the sample is contaminated and diluted with the electrophoretic buffer; accordingly, it requires dialysis and concentration, further adding to the time effort for such procedures, and ii) non-specific adsorption of sample to the dialysis membrane results in loss of recovery.

Dialysis is a molecular weight-based method of separating molecules through a semi-permeable membrane. The membrane by virtue of its composition and its porosity, allows molecules equal to or less than a particular molecular weight to cross the membrane. By using a membrane having a particular molecular weight cutoff the membrane will retain macromolecules higher than its molecular weight cutoff. On the other hand, it will allow the passage of molecules of a similar or lower molecular weight than the molecular weight cutoff of the membrane. The concentration gradient between the two sides of the dialysis membrane serves as the driving force of the process. There are four common application of dialysis membrane that are most often utilized by researchers in laboratory. 1) sample concentration, 2) sample desalting, 3) molecular separating and 4) exchanging buffer.

In a special application of dialysis, macromolecules recovered from a gel sample can be further filtered according to molecular weight. The most widely used dialysis method for such macromolecules in research laboratories uses a dialysis wherein the membrane is in the form of a tubular skin that is closed at both ends after inserting the gel sample, similar to one of the devices used for electroelution, described above. The sample solution is added to the interior of the dialysis membrane sack, which is then tied or clamp at the other end, which remained open. As with the parallel electroelution method, it requires special skill to handle the sample, as well as to tie or clamp one end of the tube to form a sack and then the other end. Furthermore leakage and the presence of air bubbles interfere with the dialysis process. Also, it is difficult to load and unload the sample from the sack because the sack is non-rigid. Many variations of this concept have been tried, albeit with little improvement.

U.S. Pat. No. 5,503,741 describes a device for dialysis of a liquid sample comprising a hermetically sealed vacant chamber formed by a gasket with dialysis membranes disposed on each side of the gasket without any supporting structure between the gasket and the membranes. The membranes are held in place over the gasket by means of inner surfaces of an external housing having windows. The gasket is impermeable to the sample being analyzed, and does not comprise an inlet opening. Rather, the gasket is penetrable by sharp means such as a needle, so that the same needs to be forcefully inserted through the gasket into the chamber in order to deliver a liquid sample thereinto. The gasket has a high memory function such that it is resealable to permit needle withdrawal without sample leakage. Thus, since the device does not have an opening into the chamber it may therefore only be used with liquid samples and not with samples contained in or carried by gels. It follows that such devices cannot be used at all for dialysis of samples contained in gels which comprise the substance of interest, and would teach away from being useful for electroelution processes conducted on a sample contained in gel. The sealed nature of the chamber is in fact a characterizing feature of this device, but this means that air needs to be evacuated from the chamber prior to injecting the liquid to be dialyzed, otherwise there is a buildup of pressure within the chamber which could serve to force some of the sample out, or could rupture the membranes. However, since the chamber is hermetically sealed, the removal of air has to be done by special means such as by using a needle to penetrate into the chamber.

The sealed aspect of the chamber is considered in this reference to prevent contamination with any substance in the air. However, since the needle has to force its way into the chamber via the gasket, any contaminants on the outside of the gasket will find their way into the chamber together with the needle.

This device has other shortcomings. Construction of the device requires the precise superposition of the membranes with respect to the gasket, on either side thereof, and then closure of two corresponding shells over the membranes and gasket. Since the membranes and gasket are substantially non-rigid components, this adds some complexity to the production process of the devices. The devices are of a non-standard shape and therefore not readily compatible with other laboratory equipment.

Other references of background interest include WO 94/01763, WO 96/26291, U.S. Pat. No. 5,200,073 and U.S. Pat. No. 4,576,702.

SUMMARY OF THE INVENTION

It is therefore an aim of the present invention to provide a device and method which overcomes the limitations of prior art electroelution/dialysis devices and methods.

Another aim of the present invention is to provide an easy and efficient new dialysis tube for separating molecules through a semi-permeable membrane system DNase, RNase and Protinase free system.

Another aim of the present invention is to provide a disposable micro-tube electroelution system, capable of conducting efficient elution of nucleic acids and protein molecules in a disposable micro-tube electrophoresis system from agarose or polyacrylamide matrix.

Another aim of the present invention is to provide a disposable micro-tube dialysis system, capable of separating molecules through a semi-permeable membrane.

It is another aim of the present invention to provide such a device that is simple to use.

It is another aim of the present invention to provide such a device that is relatively simple mechanically and thus economic to produce.

The present invention achieves these and other aims by providing a chamber for electroelution/dialysis which is closed at one end and has an opening at the other end sufficiently large to permit a sample, and in particular, a sample contained in gel, or indeed any other type of sample requiring dialysis or electroelution, for example, to be inserted. The device may optionally be closed and hermetically sealed if so desired by means of a cap. The device further comprises a pair of typically opposed portals laterally disposed with respect to the closable opening. The portals are covered with a suitable membrane, sealingly fixed on an outside surface of the housing and held in place at least with respect to the periphery of the portals by any suitable means. Typically, one membrane in tubular form services both portals and is held in overlapping sealing relationship with respect to the portals by means of an annular sealing arrangement. The device provides high yield recovery, saves time, and allows for relatively easy handling specially regarding loading and unloading of small volume of samples to be dialyzed or inserting the slice of gel containing the macromolecule sample. Furthermore, the device may optionally incorporate a suitably-shaped extension enabling the same to be compatible with any eppendorf-type stand. The device may also be made from any suitable biocompatible plastic material, rendering the device sufficiently economic to be considered disposable, thereby minimizing complexity of handling and reducing the possibility of cross-contamination. Furthermore, the device may be made from a transparent material to allow the non-intrusive inspection of its contents and thus enable a user to check the process of elution at any time.

The device also enables the electro-elution to any macromolecule from both matrices (agarose or polyacrylamide), and/or to dialyze small volume of samples.

The present invention relates to a device for accommodating at least one substance, typically in a gel, with respect to an external fluid environment at least during a predetermined process, said device comprising an impermeable housing defining a chamber adapted for accommodating therein said at least one substance, said housing having at least one inlet opening such as to provide open communication between said chamber and an outside of the device, said inlet opening being of a size sufficient to permit said at least one substance to be selectively inserted and removed from said chamber, said housing further comprising at least one first portal and at least one second portal each separate from said at least one inlet opening, said housing further comprising semipermeable membrane means associated with said at least one first portal and said at least one second portal, said semipermeable means being sealingly fixed on an outside surface of said housing such that fluid communication between said chamber and said external fluid environment via at least one first portal and at least one second portal is through said membrane means.

In the preferred embodiment, said at least one first portal and said at least one second portal are disposed in laterally opposed directions with respect to a longitudinal axis of the device. The housing is substantially cylindrical having first and second longitudinally opposed ends and a substantially cylindrical side wall, and said at least one first portal and said at least one second portal are comprised on said cylindrical side wall. Typically, said at least one first portal and said at least one second portal are disposed at about 180° to one another with respect to a longitudinal axis of the said housing.

In the preferred embodiment, said inlet opening is comprised at said first longitudinal end of said housing, and the inlet opening comprises a flange radially extending therefrom. The second longitudinal end of said housing is closed, and optionally further comprises a spike extending longitudinally into said chamber from said closed end, said spike being particularly adapted for holding said at least one substance in said chamber when said at least one substance is in solid or gel form.

Preferably the device comprises a cap for reversibly closing said inlet opening. In a first embodiment, the cap comprises a plug portion adapted for insertion into said open end and the plug comprises a rib adapted for sealing engagement with a complementary recess within said housing. The cap may further comprise a flange radially extending from said plug portion. Advantageously, the cap comprises indicia marked on an external surface thereof, and the indicia may comprise the characters "+" and "−", typically laterally aligned with said at least one first portal and said at least one second portal, respectively.

A second embodiment of the cap comprises a plug portion adapted for reversible screwable (threaded) sealable engagement with respect to said open end, said plug portion comprising an external screw thread adapted for sealing helical engagement with a complementary internal screw thread within said housing. The cap may further comprise a flange radially extending from said plug portion, and the cap may comprise a finger gripping knurled cylindrical surface.

In the preferred embodiment, said membrane means comprises a substantially tubular sleeve having first and second longitudinal ends and made from a semipermeable membrane material, wherein said first and second longitudinal ends of the said sleeve are suitably sealing clamped onto said outside surface by suitable clamping means at least at a first and a second sealing station at each longitudinal end of said at least one first portal and said at least one second portal. Preferably, said clamping means comprises a substantially tubular clamping member adapted for sliding over said sleeve when the same is positioned over said housing, and comprising sealing means to sealingly lock said sleeve with respect to said sealing stations, said clamping member further comprising at least one third portal and said at least one fourth portal complementary to and adapted to aligned with said at least one first portal and said at least one second portal, respectively. The sealing means may comprise, at each said sealing station, a first circumferential rib in an inner surface of said clamping member and a second and a third circumferential ribs on the said outside surface of said housing defining a valley portion therebetween for aligning and accommodating therein said first rib when a portion of said sleeve is interposed between said first rib and said second and third ribs.

Optionally, the housing or the clamping member may further comprises a foot member axially extending therefrom in a direction opposed to that of said chamber. The foot member may be conical or any other suitable shape or may comprise a plurality of flanges extending radially and longitudinally from a longitudinal axis of said housing.

The device, in particular the housing, cap and clamping member, are each made from a biocompatible material, in particular a material chosen from polypropylene, polyethylene, or any other suitable thermoplastic material. Similarly the sleeve is made from a biocompatible material, in particular a material chosen from, cotton linters or cellulose, cellulose acetate, polysulfone, polycarbonate, polyethylene, polyolefin, polypropylene, and polyvinylidene fluoride.

The device may be associated with an external fluid environment comprising solution suitable for use as a running buffer for DNA, RNA or proteins, in particular such a solution chosen from TBE, TAE or protein running buffer solution.

The device may be used in an electroelution process, the device typically accommodating a gel slice containing at least one macromolecule species of interest.

Additionally or alternatively, the device may be used in a dialysis process. By way of examples, the said at least one substance may comprise a solution of antibodies with sodium azide, and said external fluid environment comprises a suitable buffer that does not comprise sodium azide; or said at least one substance comprises a solution of DNA with buffer of low or high pH, and said external fluid environment comprises a suitable solution having a pH of between about 7.0 and about 8.0, or said at least one substance comprises a solution of protein with about 20% glycerol, and said external fluid environment comprises a suitable buffer that does not comprise glycerol.

The present invention also relates to a tray for mounting thereto a plurality of such devices, said tray comprising a base and a plurality of stands for holding said devices. In the preferred embodiment, each said stand may comprise a pair of facing resilient clamping members cantilevered from said base and which may be elastically prised apart to allow a corresponding said device to be inserted therebetween, and to subsequently provide a clamping force on said corresponding device when disposed therebetween. The tray may be made from any suitable material including Azetal. Optionally, the tray further comprises opposed uprights running substantially the length of the tray perpendicular to the longitudinal axis of each said device mounted on said tray. Optionally, the tray further comprising at least one aperture in said base for facilitating the flow of water or ionic solution in a running chamber associated with said tray.

The tray optionally further comprises suitable attachment for attaching said tray to a second said tray. The attachment means may comprise a set of ridges on one said upright of one said tray, which are adapted for aligning and intermeshing with corresponding seats comprised in the corresponding upright of the other said tray.

BRIEF DESCRIPTION OF FIGURES OF THE DRAWING

FIG. 11 (b) shows half the tray assembly of FIG. 11 (a) with a plurality of devices mounted thereon.

DETAILED DESCRIPTION OF PREFERRED EMBODIMENTS

The present invention is defined by the claims, the contents of which are to be read as included within the disclosure of the specification, and will now be described by way of example with reference to the accompanying Figures.

The present invention relates to a device for accommodating at least one substance—particularly a macromolecule of interest—with respect to an external fluid environment at least during a predetermined process. Such a process may be electroelution of at least one substance such as macromolecules of DNA, RNA and proteins from semi-dry matrices such as agarose or polyacrylamide gels to a fluid solution in the device, for example. In such a process, the fluid in the device is in communication with an external fluid environment which enables an electric field to be set up and used as a power source for eluting the macromolecules from the gel. Additionally or alternatively, the process may also comprise dialysis of a substance contained in the device with respect to the external fluid.

In its simplest form, the device of the present invention comprises an impermeable housing defining a chamber adapted for accommodating therein said at least one substance, which is typically but not exclusively contained in a gel. The housing has at least one inlet opening such as to provide open communication between the chamber and an outside of the device, the inlet opening being of a size sufficient to permit the substance to be selectively inserted and removed from said chamber, and the housing further comprises at least one first portal and at least one second portal each separate from said at least one inlet opening. The housing further comprises semipermeable membrane means associated with said at least one first portal and said at least one second portal, said semipermeable means being sealingly fixed on an outside surface of said housing such that fluid communication between said chamber and said external fluid environment via at least one first portal and at least one second portal is through said membrane means.

Such a device is preferably disposable, but may also be re-usable for a host of applications. The term "disposable" in the present application means that the devices are designed (in corresponding embodiments) to be thrown away or otherwise disposed off after one use with only negligible economic loss. Negligible economic loss herein means an economic loss per device of the same order as the range of per unit costs associated with semipermeable membranes and regular eppendorf-type tubes, for example.

Referring to the Figures, FIGS. 1 to 10 illustrate a preferred embodiment of the present invention. The device, designated by the numeral (1), typically comprises a housing or inner tube (20), a membrane means (60), and optionally a cap (10).

Figure 1:
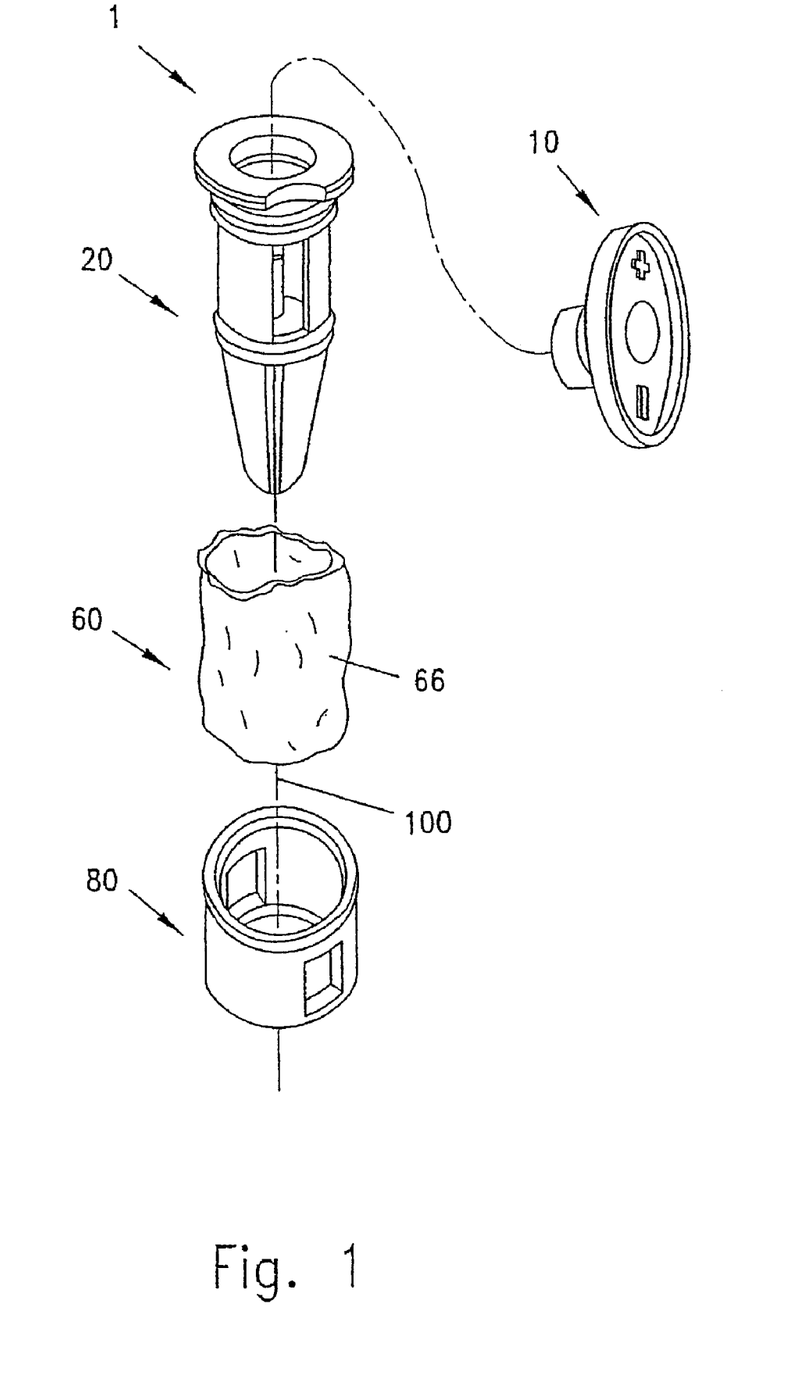
FIG. 1 shows in exploded perspective sectional view the main elements of a preferred embodiment of the present invention.
Figure 2A:
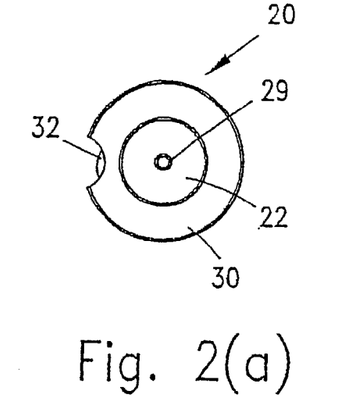
FIGS. 2(a), 2(b) and 2(c) shows in front view, side view and top view, respectively, the inner tube of the embodiment of FIG. 1.
Figure 2B:
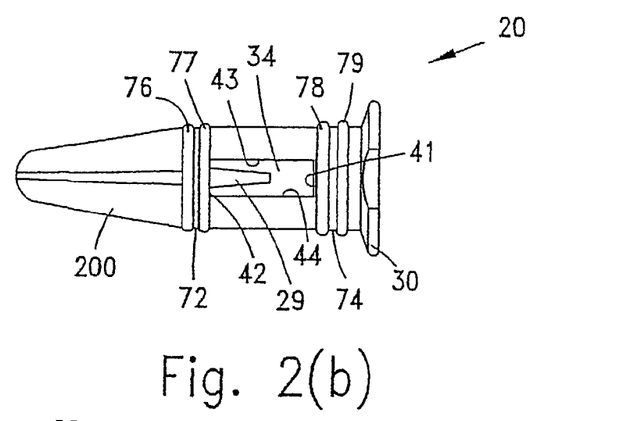
Figure 2C:
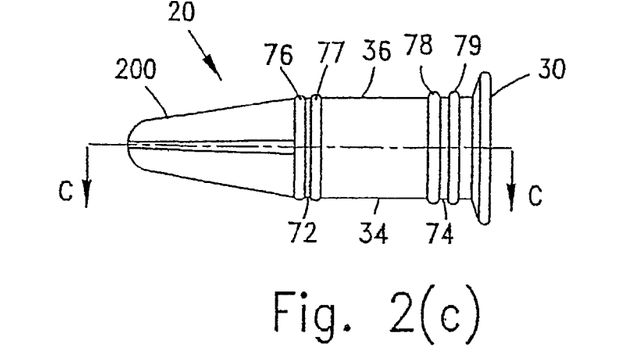
Figure 3:
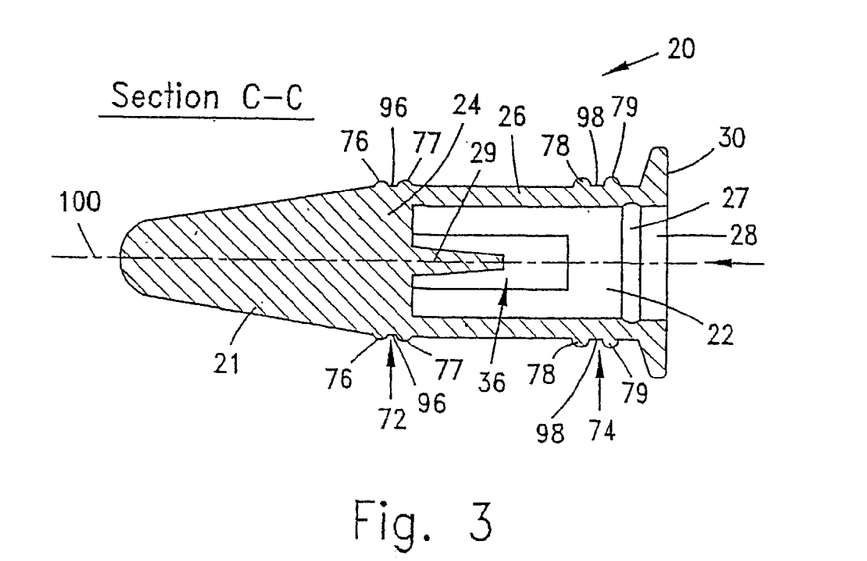
FIG. 3 shows in side elevational cross-sectional view, the embodiment of FIG. 2(c) taken along C—C.
Figure 4A:
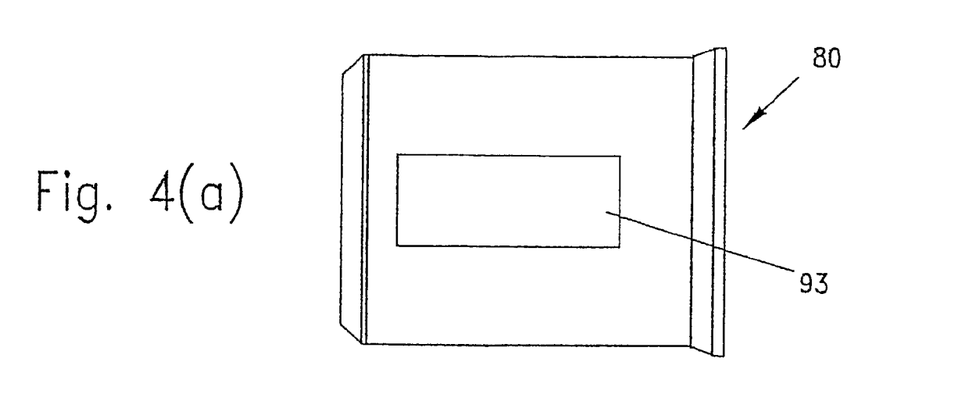
FIGS. 4(a) and 4(b) shows in side view and top view, respectively, the clamping member of the embodiment of FIG. 1.
Figure 4B:
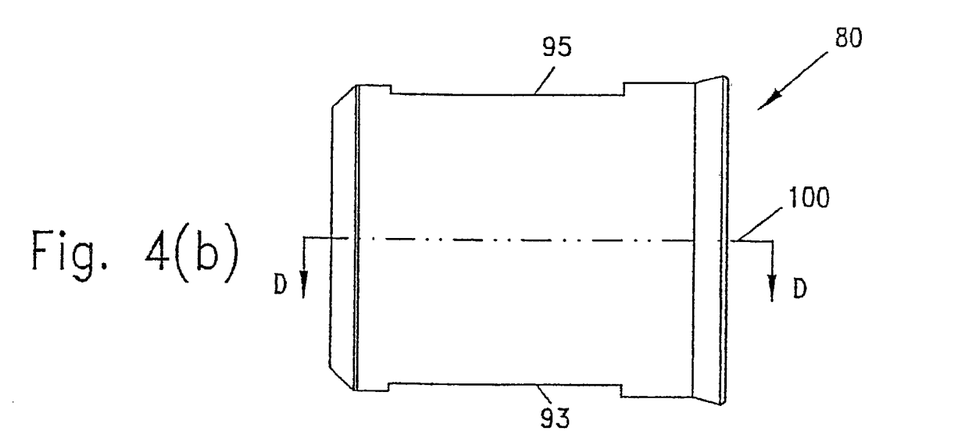
Figure 5:
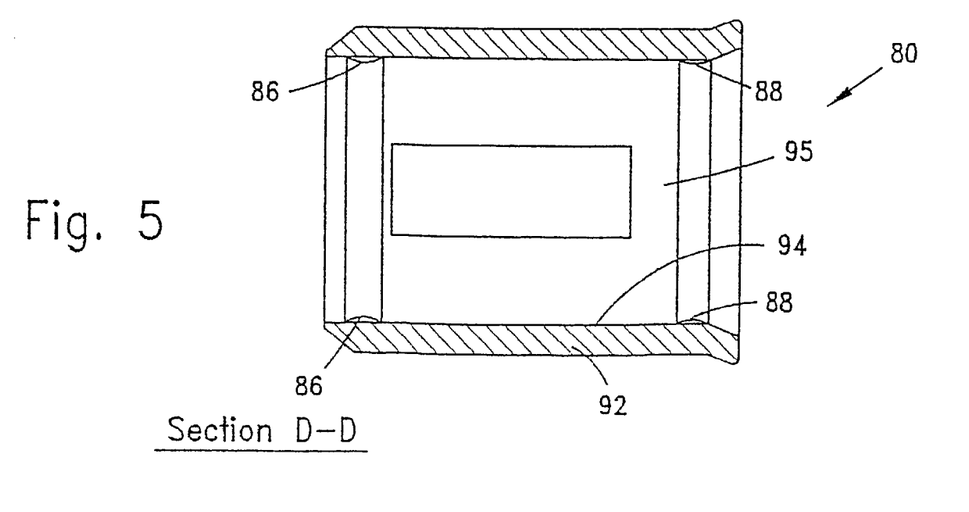
FIG. 5 shows in side elevational cross-sectional view, the embodiment of FIG. 4(b) taken along D—D.
Figure 6A:
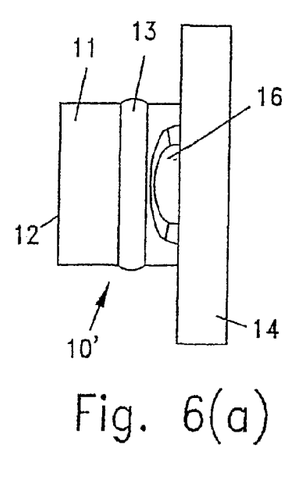
FIGS. 6(a), 6(b) and 6(c) shows in side view, front view and rear view, respectively, the cap of the embodiment of FIG. 1.
Figure 6B:
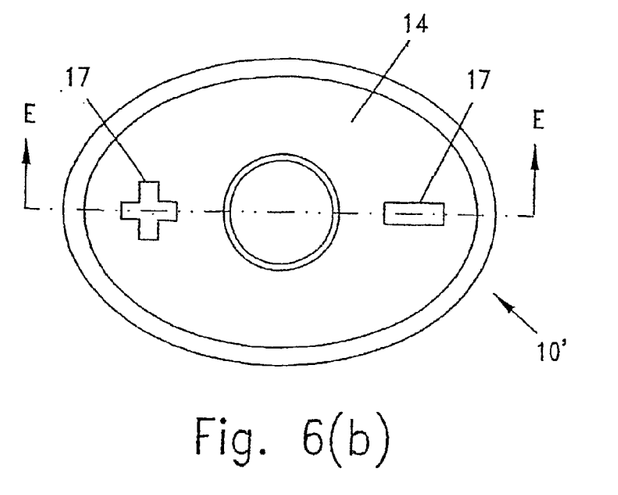
Figure 6C:
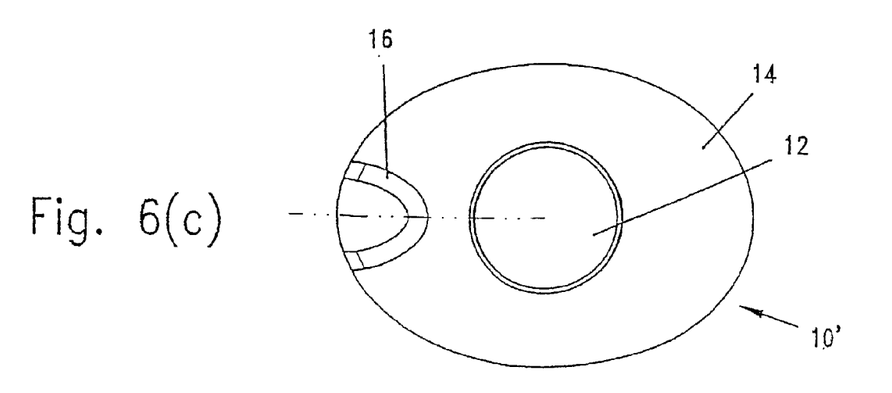
Figure 7:
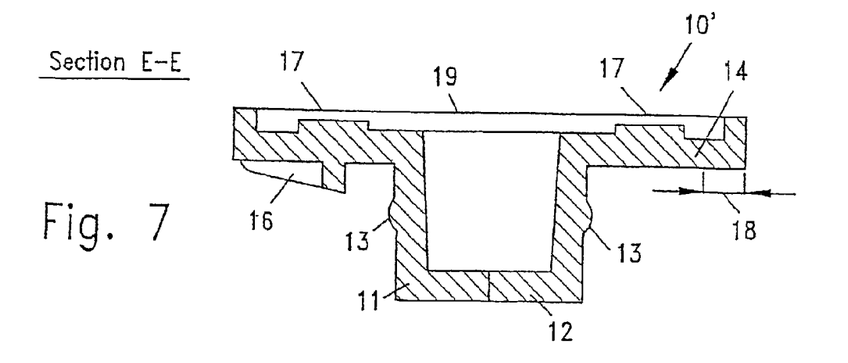
FIG. 7 shows in top elevational cross-sectional view, the embodiment of FIG. 6(b) taken along E—E.
Figure 8:
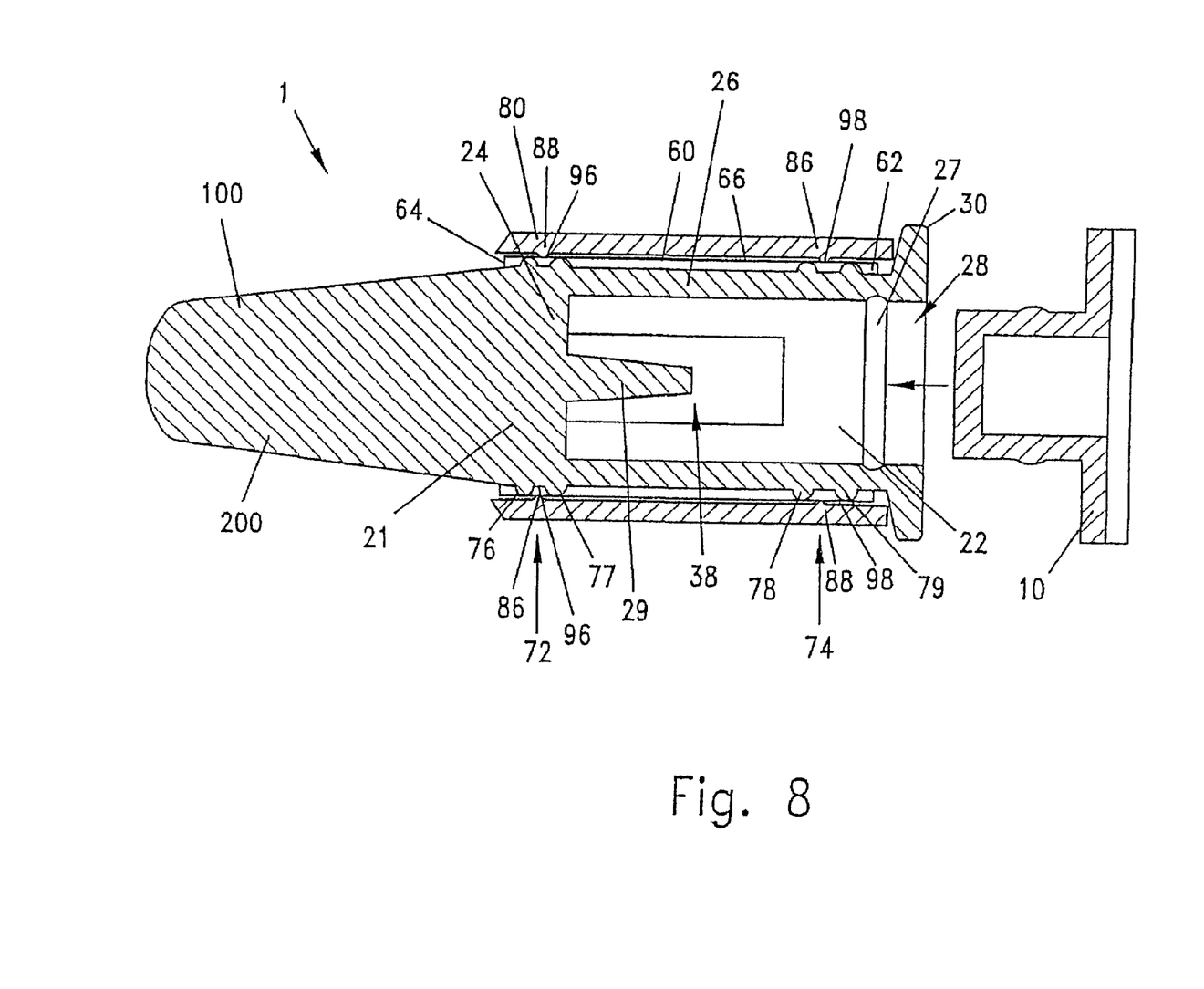
FIG. 8 shows in side elevational cross-sectional view the embodiment of FIG. 1 partially assembled.
Figure 9A:
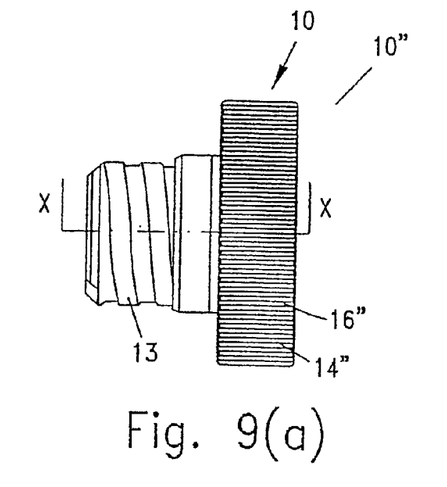
FIGS. 9(a) and 9(b) shows in side view and front view, respectively, a second embodiment of the cap.
Figure 9B:
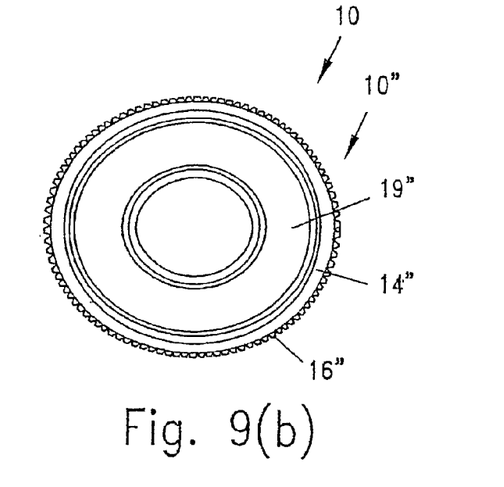
Figure 10A:
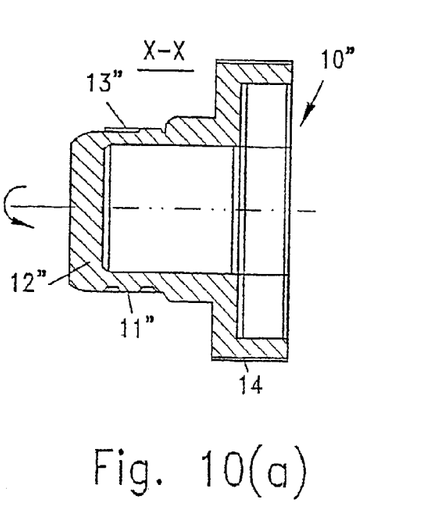
FIG. 10 shows in top elevational cross-sectional view, the embodiment of FIG. 9(a) taken along X—X, including the corresponding cross-sectional view inner tube of the device adapted to receive this embodiment of the cap.
Figure 10B:
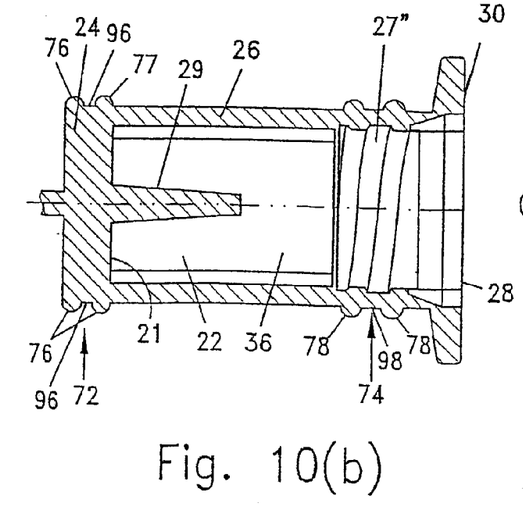

Referring in particular to FIGS. 1, 2(*a*), 2(*b*), 3 and 8, the housing or inner tube (20) is impermeable, i.e., it is made from an impermeable material or has an impermeable coating or the like, such that the walls of the housing themselves are impermeable, though of course any openings in the housing are themselves not impermeable. The inner tube (20) has an open first end (28) and a second end (21) comprising an end wall (24), and further comprises an inner processing chamber (22) enclosed by said end wall (24) and a cylindrical side wall (26) joined thereto. While the preferred embodiment comprises a closed end wall (24), in other embodiments, the inner tube (20) may have a corresponding closed end formed from the side walls, which in such cases be formed such as to provide a conically shaped inner chamber having its apex at the closed end, for example, rather than as the cylindrical element of the preferred embodiment. In the preferred embodiment, said open end (28) comprises an annular flange (30) radially extending outwardly from the side wall (26). The flange (30) comprises a recess (32), preferably arcuate in form in the plane of the flange (30), and extending substantially the full width thereof. The purpose of the recess (32) will be described hereinbelow. The side wall (26) comprises substantially opposed portals (34), (36), providing lateral fluid communication from outside the inner tube (20) on one side thereof, through the inner chamber (22), and to another side of the inner tube (20). In the preferred embodiment, the portals (34), (36) are of substantially the same size and disposed one opposite the other, i.e., at about 180°, with respect to the longitudinal axis (100) of the inner tube (20). Further, in the preferred embodiment the portals (34), (36) are substantially rectangular in profile taken over the cylindrical surface of the said sidewall (26), each portal (34), (36) comprising arcuate longitudinally opposed end walls (41), (42), and substantially linear longitudinal walls (43) and (44). In other embodiments, the portals (34), (36) may be sized differently one from the other, and may have any desired shape, and may also be longitudinally displaced one from the other or disposed one from the other at angles other than 180° with respect to the central axis (100), so long as reasonable transverse fluid communication through the inner tube (20) via the portals (34), (36) is still ensured. Optionally, other embodiments of the device the single portal (34) and/or the single portal (36) may be replaced with a plurality of portals, having any suitable profile including orifices, slits, a mesh arrangement and so on.

Optionally, the inner chamber (22) may comprise a spike (29) extending longitudinally from the end wall (24) into the chamber (22), the spike (29) being particularly useful for seating and properly aligning a gel slice with respect to portals (34), (36).

The portals (34), (36) are each sealingly covered by a suitable membrane means (60). The membrane means (60) comprises a material that enables separation of a first substance from a second substance to be performed on a sample placed within the inner chamber (22). Such separation relates in particular to molecules having molecular weights within one range of molecular weights being separated from molecules having molecular weights within a second range of molecular weights. In particular, such controlled separation may involve processes such as dialysis and electroelution. Thus, for electroelution processes, the membrane means (60) may comprise any suitable semipermeable membrane material that enables ionic and molecular communication between one side of the membrane means (60) and the other side thereof, when the membrane means (60) is in contact with a suitable buffer solution on either side of the membrane means (60). The semipermeable membrane only allows molecules up to a predetermined size to pass through, larger molecules being blocked by the membrane. Thus, with respect to electroelution, the membrane means (60) is chosen so as to permit molecules smaller than the target macromolecules to pass through the membrane and thus be removed from the inner chamber (22), the target macromolecules being the macromolecules which are desired to be harvested from the gel slice. Thus, a membrane is chosen having a cut-off suitable for electro elution of any size fragment of double strand or single strand DNA or RNA, or proteins. Similarly, for dialysis uses, the membrane means (60) also comprises a semipermeable membrane material that enables molecules of molecular weight lower than a particular threshold to pass therethrough and further enables the flow of ions from a hypertonic solution thereof to a hypotonic solution, to provide the required tonicity within the inner chamber (22), while enabling target macromolecules to be retained therein.

The membrane means (60) may comprise a pair of membrane patches which are sealingly clamped or otherwise sealingly fixed over the corresponding portals (34), (36). Preferably, and in the preferred embodiment, the membrane means (60) is in the form of a substantially cylindrical continuous sleeve (66) of a membrane material having longitudinally opposed open ends (62), (64). The sleeve (66) comprises a diameter greater than the external diameter of the inner tube (20), enabling the sleeve (66) to be slid over the inner tube (20) such as to completely cover the portals (34), (36). Typically, this is done in a direction from the longitudinal end of the inner tube (20) that comprises end wall (24). The sleeve (66) is then sealingly clamped over the inner tube (20) at sealing stations (72), (74) disposed on either longitudinal side of the portals (34), (36). Preferably, and in the preferred embodiment, the side wall (26) comprises, at each of the sealing stations (72), (74), a pair of longitudinally spaced circumferential ribs, (76), (77), and (78), (79), respectively, and the inner diameter of the sleeve (66) is nominally equal to, but may be slightly greater than or smaller than, the external diameter of the ribs (76), (77), (78), (79). Clamping of the sleeve (66) may be accomplished in a number of ways. For example, suitable rubber bands having a non-stressed inner diameter slightly smaller than the external diameter of the inner tube (20) may be individually elastically stretched and hooped over the sleeve (66) and inner tube (20), and then released at the said stations (72), (74), thereby contracting and holding the sleeve (66) in position with respect to the inner tube (20). Alternatively, suitable pieces of string, tape, thread or the like may be tied or otherwise held fast in a loop around the sleeve (66) and inner tube (20) at each of the stations (72), (74). In each case, though, at least a part of each of the portions of the sleeve (66) that are superposed over the portals (34), (36) remain exposed to the outside. Alternatively, suitable clamps having suitably dimensioned arcuate clamping surfaces may be used. Alternatively, the sleeve (66) may be comprised of an elastic stretchable material, having a diameter slightly smaller than that of the sealing stations (72), (74), when in the unstressed state, thereby enabling the sleeve (66) to be sealingly secured thereat by virtue of the tension developed in the sleeve when hooped over the sealing stations (72), (74). In the preferred embodiment, the sleeve (66) is sealingly clamped over the inner tube (20) by means of a tubular clamping member (80).

Referring in particular to FIGS. 4(a), 4(b), 5 and 8, the clamping member (80) is adapted to be slid over the sleeve (66) when the latter is positioned over the inner tube (30), and to sealingly lock the sleeve (66) with respect to the sealing stations (72), (74). The clamping member (80) is typically tubular in form and thus comprises a cylindrical wall (92) having an inner cylindrical surface (94). The inner diameter of the cylindrical wall (92), i.e., of the surface (94), is preferably nominally equal or slightly greater than the diameter of the sleeve (66) at the sealing stations (72), (74), i.e., the diameter of the corresponding ribs (76), (77), (78), (79), increased by twice the thickness of the sleeve (66). The clamping member (80) further comprises a pair of ribs (86), (88) disposed on the surface (94). The ribs (86), (88) are longitudinally spaced one from the other such that when the clamping member (80) is slid and properly positioned over the sleeve (66) and inner tube (20), the ribs (86) and (88) are disposed at the sealing stations (72), (74), respectively, and particularly in the spaces (96), (98) respectively, between the pairs of ribs (76), (77) and (78), (79), respectively. The dimensions of the inner tube ribs (76), (77) and (78), (79), and of the clamping member ribs (86), (88) are chosen within close tolerances such as to provide a snap fit between corresponding sets of said ribs ((86) and (76), (77)), and ((88) and (78), (79)) respectively, when the sleeve (66) is interposed between corresponding ribs of each set, thereby sealing the sleeve (66) at the sealing stations (72), (74). The longitudinal spacing (98) between ribs (78), (79) may be set to be larger than the longitudinal spacing (96) between ribs (76), (77) (or indeed vice versa) to ensure that ribs (86) and (88) always coincide with spaces (96), (98), respectively, when the device (1) is assembled. This helps to take account of reasonable dimensional deviations that may arise in the longitudinal spacing of ribs (86), (88) due to manufacturing errors, for example. The clamping member (80) further comprises a pair of secondary portals (93), (95), each for providing lateral fluid communication from the outside to the inside of the clamping member (80). The secondary portals (93), (95) are sized and disposed on the cylindrical wall (92) such as to be juxtaposed with respect to the portals (34), (36) of the inner tube (20) when the clamping member (80) is sealingly clamped over the sleeve (66) and inner tube (20). In the preferred embodiment, the secondary portals (93), (95) are preferably similar in shape and dimensions to the portals (34), (36) of the inner tube (20).

The device (1) further comprises a cap (10) sealingly closing open end (28). Referring in particular to FIGS. 1, 6(a), 6(b), 6(c), 7 and 8, a first embodiment of the cap (10') comprises a tubular plug portion (11) adapted to be inserted into said open end (28), and comprises an external rib (13) adapted for engagement with a complementary recess (27) in said side wall (26) to form a substantially impermeable snap fit arrangement. The plug portion (11) is closed at a first longitudinal end (12) thereof, and comprises a flange (14) at the other longitudinal end thereof, radially extending from the plug portion (11). The flange (14) preferably comprises an elliptical profile, having a minor axis approximately equal to the diameter of flange (30) of the inner tube (20), and a major axis about 20% to about 40% larger than the minor axis. The flange (14) comprises a substantially arcuate projection (16) that is adapted to be received in recess (32) when the cap (10') is sealingly fitted to inner tube (20). The arcuate projection (16), and to a lesser extent the overhang (18) of the other transverse end of the flange (14) with respect to the flange (30) of the inner tube (20), greatly facilitates removal of this embodiment of cap (10') from the inner tube (20) when it is desired to open the same. Preferably, the major axis of the flange (14) is aligned with the portals (34), (36). Optionally, and preferably, the outer face (19) of the cap (10') comprises indicia (17), marked "+" and "−", which may be embossed, etched, printed or otherwise marked thereon. These indicia (17) enable the user to easily align the device (1) in an electroelution running chamber in the correct direction, such that the "−" and the "+" indicia are respectively in the direction of the cathode and the anode. This is of particular importance if the device (1) needs to be temporarily removed from the electroelution running chamber and reintroduced with the same orientation.

Alternatively, and referring to FIGS. 9(a), 9(b), 10(a) and 10(b), a second and preferred embodiment of the cap (10") is adapted to sealingly close open end (28) by a substantially helical screwing action. The second embodiment of the cap (10") comprises a tubular plug portion (11") adapted to be inserted into said open end (28), and comprises an external screw thread (13") which is adapted for helical engagement with a complementary internal screw thread (27") in said side wall (26) to form a substantially impermeable screw fit arrangement. The plug portion (11") is closed at a first longitudinal end (12") thereof, and comprises a flange (14") at the other longitudinal end thereof, radially extending from the plug portion (11"). The flange (14") preferably comprises a circular profile, and preferably comprises a finger gripping knurled cylindrical surface (16") which facilitates removal of this embodiment of cap (10") from the inner tube (20) when it is desired to open the same. By twisting the cap (10") selectively clockwise or anticlockwise, the cap (10") is sealingly closed or opened, respectively, with respect to the inner tube (20).

As with the first embodiment of the cap (10'), optionally, and preferably, the outer face (19") of the second embodiment of the cap (10") comprises indicia (not shown), marked "+" and "−". These indicia may be embossed, etched, printed or otherwise marked thereon, preferably such that when the cap (10") is at the end of its axial travel into the inner tube (20) and cannot rotate any more relative thereto, and thus these indicia are situated in a repeatable position relative to the inner tube (20), typically circumferentially aligned with portals (34) and (36). These indicia enable the user to easily align the device (1) in an electroelution running chamber in the correct direction, such that the "−" and the "+" indicia are respectively in the direction of the cathode and the anode. This is of particular importance if the device (1) needs to be temporarily removed from the electroelution running chamber and reintroduced with the same orientation.

Alternatively, for either the first or second embodiment of the cap, (10') and (10") respectively, the outer surface of the clamping member (80), and/or the outer surface of the inner tube (20), may optionally comprise indicia (not shown), marked "+" and "−", which may also be embossed, etched, printed or otherwise marked thereon. As before, these indicia enable the user to easily align the device (1) in an electroelution running chamber in the correct direction, such that the "−" and the "+" indicia are respectively in the direction of the cathode and the anode.

Optionally, and preferably, the device further comprises a foot member (200) preferably integrally attached to the second end (21) of the said inner tube (20). The foot member (200) comprises, in the preferred embodiment, a cruciform transverse cross-section profile, having a number—typically 2, 3, 4 or more—of radially and longitudinally extending adjacent flanges (210) in substantially radial arrangement with respect to one another with respect to the axis (100). Alternatively, for example, the foot member may be conical, frustroconical, pyramidal, or indeed similar in profile to the closed end of a regular eppendorf tube, or indeed any other suitable shape such as to enable the device (1) to be held in any desired position (by suitable clamps, a stand or an Eppendorf style stand, for example), without interfering with the membrane sleeve (66), secondary portals (93), (95), or cap (10). This is of particular importance when the device (10) is used for electroelution, and must be oriented in a particular direction with respect to an electric field. Each flange (210) optionally comprises a transverse profile similar to the external profile of a regular Eppendorf-type tube, rendering the device (1) compatible with a host of laboratory stands and equipment commonly used with Eppendorf tubes. In this way, the foot member (200) allows convenient handling of the device (1), in particular the loading/unloading of gel slices, and the delivery/removal of small volumes of solutions to be dialyzed, since the device (1) can be stood on its end in a regular stand, with the said open end (28) uppermost.

Alternatively, the device (10) comprises a foot member (not shown) preferably integrally attached to the end of the said clamping member (80) that is closest to said end wall (24) of the inner tube (20) when engaged in place. Such a foot member for said clamping member (80) may be similar to the foot member (200) as described with respect to the inner tube (20), mutatis mutandis.

The cap (10), inner tube (20) and clamping member (80) are each preferably made from a medically compatible material, preferably a plastic material, and also preferably manufactured each as an integral, optionally molded, item. Optionally, the cap (10), inner tube (20) and clamping member (80) are each made from a disposable but stable material that does not deteriorate with the passage of time, and is thus suitable when the device (1) is used for processing toxic or other dangerous substances. However, when the device (1) is intended for use with non-toxic or other non-dangerous substances it may be made advantageously from an environmentally friendly material, possibly even a biodegradable or recyclable material particularly if the substances to be processed in the device (1) are likewise biodegradable or recyclable. Typically, the cap (10), inner tube (20) and clamping member (80) are each made from a suitable plastic material such as polypropylene, polyethylene, or any suitable thermoplastic material.

Depending on the specific use, the membrane sleeve (66) is derived from cotton linters. The cotton or cellulose is dissolved in a solution and spread into flat sheets or extruded into tubes. The sheets are then treated with glycerin (to prevent the pores from collapsing) and air dried at a certain temperature and pressure to form a rigid membrane. When required for use, the rigid membrane is treated with special solutions known in the art that render the membrane flexible. The membrane may be made from any suitable natural or synthetic material including regenerated cellulose, cellulose acetate, polysulfone, polycarbonate, polyethylene, polyolefin, polypropylene and polyvinylidene fluoride.

The pore structure of a cellulosic membrane is symmetric and allows small molecules to migrate in either direction. A regenerated cellulose membrane is modified cellulose, which optimizes the pore structure, making it ideal for experimental purposes.

Figure 11A:
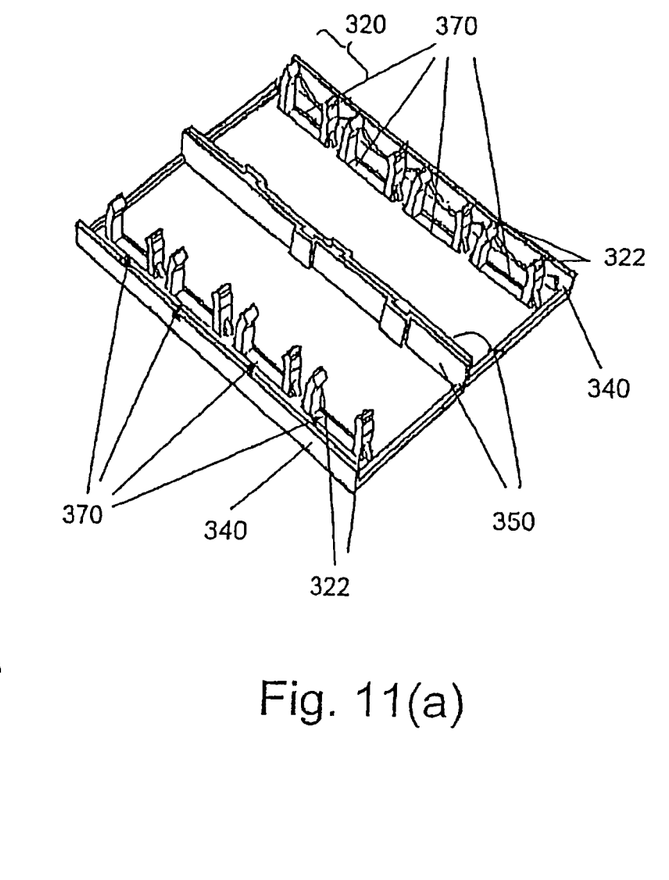
FIG. 11(a) shows in perspective view a tray assembly for supporting a plurality of devices according to the preferred embodiment of the present invention.
Figure 11B:
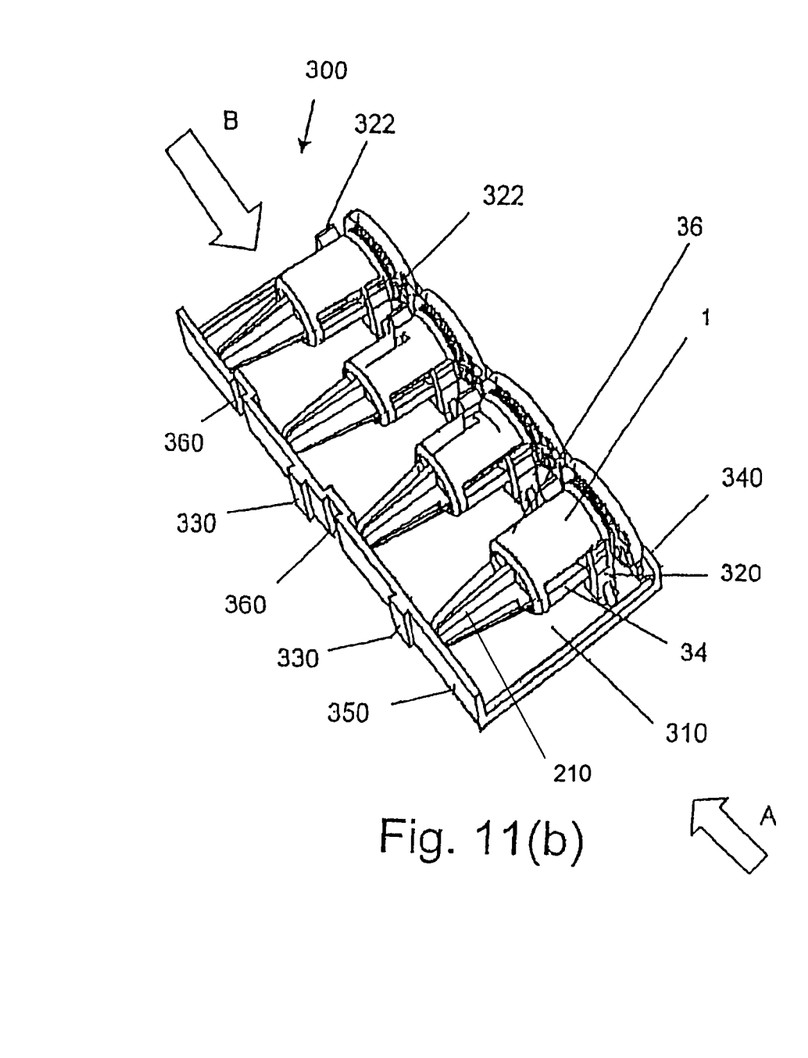

Referring to FIG. 11, a plurality of devices (1) may be simultaneously mounted onto a tray (300), which comprises a base (310), and a plurality of stands (320) for holding the devices (1). The stands (320) comprise a pair of facing resilient clamping members (322) cantilevered from the base (310), and which may be elastically prised apart to allow a device (1) to be inserted therebetween, and subsequently provide a clamping force on the device (1) when disposed therebetween. The device (1) is secured in the tray (300) with its portals (34), (36) in the direction of arrows A, B, such as to align the portals (34), (36) with the anode and cathode of the running chamber. The tray (300) may be made from any suitable material, such as Azetal, which is denser than water and thus facilitates immersion of the tray (300) in the buffer solution of the running chamber. Optionally, the tray comprises uprights (340), (350) running the length of the tray (300) parallel to the direction of arrows A, B. Advantageously, apertures (370) are provided in base (310) for facilitating the flow of water or ionic solution in the running chamber.

Optionally, a second tray (300') substantially similar to the first tray (300) may be attached to said tray (300) by any suitable attachment means. One form of such attachment means comprises a set of ridges (330) on one upright (350) of the first tray, which are aligned with and intermesh 'with corresponding seats (360) in the corresponding upright (350') of the second tray (300').

The device (1) may be used with or without the cap (10). If used without the cap (10), the device (1) is only partially immersed in the liquid medium of interest such that the open end (28) is above the surface of the liquid, and therefore liquid communication between the chamber (22) and the external liquid medium is only via the membrane means (60) and portals (34), (36). This is particularly facilitated by the foot members (200) which enable the devices (1) to be mounted on a stand, typically an Eppendorf-tube compatible stand, in an upright position having open end (28) uppermost. Alternatively, the device (1) may be fitted with cap (10) such as to hermetically seal the open end (28). In such a case, the device (1) may be fully immersed in the liquid medium of interest, and again liquid communication between the chamber (22) and the external liquid medium is only via the membrane means (60) and portals (34), (36).

Typically, the device (1) is connected to two external ions exchange chambers or immersed in an exchange buffer, and the inner chamber (22) provides an environment to conduct the electro-elution or dialysis for the gel slice that comprises the macromolecules of interest. The inner chamber (22) is closed by means of the cap (10), and the device (1) is then immersed in an external ion exchange chambers for providing a driving force for electro-elution, by connecting the apparatus to external electrical power source. Alternatively, the device (1) may be immersed in an exchanging buffer for dialysis, separating macromolecules by concentration gradient.

Additionally or alternatively, the device may be used in a dialysis process. By way of examples, the said at least one substance may comprise a solution of antibodies with sodium azide, and said external fluid environment comprises a suitable buffer that does not comprise sodium azide; or said at least one substance comprises a solution of DNA with buffer of low or high pH, and said external fluid environment comprises a suitable solution having a pH of between about 7.0 and about 8.0, or said at least one substance comprises a solution of protein with about 20% glycerol, and said external fluid environment comprises a suitable buffer that does not comprise glycerol.

The device may be used as follows. Using a sharp scalpel or razor blade, a slice of agarose or acrylamide containing the band of interest is cut from the gel body, and mounted at the spike (29) in the inner chamber (22). The inner chamber (22) is filled with water (say, about 0.8 ml) or any desired buffer, and then closed by means of cap (10). The device (1) is then immersed in 1× TAE in an electrophoresis tank. An electric current is then passed through the device (10) (typically 80 V for about 10–30 minutes). During this time, the DNA, RNA or protein is electroeluted out of the gel and onto the water in the inner chamber (22). The process can be conveniently monitored with an ultraviolet lamp. The polarity of the current is then reversed (typically for a duration of about 20 seconds to release the DNA, RNA or protein from the wall of the dialysis membrane (66). The device (1) is then recovered from the electrophoresis chamber, and the side of the inner chamber (22) where the DNA, RNA or protein accumulated is gently pipetted to remove these molecules from the wall. The device (1) is then opened via said cap (10), and the water therein is carefully transferred to a clean 1.5-ml microfuge tube and the DNA, RNA or protein is precipitated. For example, the salt concentration is adjusted with sodium acetate (0.3 M, pH 5.2, final concentration) or ammonium acetate (2.0–2.5 M, final concentration). Then, about 0.7–1.0 volumes of room-temperature isopropanol is added to the water and mixed well. The sample is then centrifuged immediately at about 10000–15000× g for 15–30 minutes at 4° C. The supernatant is then carefully decanted without disturbing the pellet. The pellet is then washed by adding 1 ml of room temperature 70% ethanol, and then centrifuged at 10000–15000× g for 5–15 minutes at 4° C. The supernatant is carefully decanted without disturbing the pellet, which is then air-dried for about 5–20 minutes. The DNA or RNA is then redissolved in a suitable buffer.

For dialysis, the sample is placed in the device (1), which is then closed via cap (10). The device (1) is then immersed in a large volume of special buffer for 1.5–3 hours. The sample is then transferred to a clean tube.

While in the foregoing description describes in detail only a few specific embodiments of the invention, it will be understood by those skilled in the art that the invention is not limited thereto and that other variations in form and details may be possible without departing from the scope and spirit of the invention herein disclosed.

What is claimed is:

1. A device for accommodating at least one substance with respect to an external fluid environment at least during a predetermined process, said device comprising an impermeable inner member defining a chamber adapted for accommodating therein said at least one substance, said inner member having at least one inlet opening such as to provide open communication between said chamber and an outside of the device, said inlet opening being of a size sufficient to permit said at least one substance to be selectively inserted and removed from said chamber, said inlet opening being bound on all sides by said inner member, said inner member further including at least one first portal and at least one second portal each separate from said at least one inlet opening, said device further comprising semipermeable membrane means associated with said at least one first portal and said at least one second portal, said semipermeable membrane means being sealingly fixed on an outside surface of said inner member such that fluid communication between said chamber and said external fluid environment via at least one first portal and at least one second portal is through said membrane means.

2. A device as claimed in claim 1, wherein said at least one first portal and said at least one second portal are disposed in laterally opposed directions with respect to a longitudinal axis of the inner member.

3. A device as claimed in claim 2, wherein said inner member is substantially cylindrical having first and second longitudinally opposed ends and a substantially cylindrical side wall.

4. A device as claimed in claim 3, wherein said at least one first portal and said at least one second portal are comprised on said cylindrical side wall.

5. A device as claimed in claim 4, wherein said at least one first portal and said at least one second portal are disposed at about 180° to one another with respect to a longitudinal axis of the said inner member.

6. A device as claimed in claim 3, wherein said inlet opening is comprised at said first longitudinal end of said inner member.

7. A device as claimed in claim 6, wherein said inlet opening comprises a flange radially extending therefrom.

8. A device as claimed in claim 3, wherein said second longitudinal end of said inner member is closed.

9. A device as claimed in claim 8, further comprising a spike extending longitudinally into said chamber from said closed end, said spike being particularly adapted for holding said at least one substance in said chamber when said at least one substance is in solid or gel form.

10. A device as claimed in claim 8, wherein said inner member further comprises a foot member axially extending from said second closed end in a direction opposed to that of said chamber.

11. A device as claimed in claim 10, wherein said foot member comprises a plurality of flanges extending radially and longitudinally from a longitudinal axis of said inner member.

12. A device as claimed in claim 10, wherein said foot member is substantially conical.

13. A device as claimed in claim 3, further comprising a cap for reversibly closing said inlet opening.

14. A device as claimed in claim 13, wherein said cap comprises a plug portion adapted for insertion into said inlet opening and comprises a rib adapted for sealing engagement with a complementary recess within said inner member.

15. A device as claimed in claim 14, wherein said cap further comprises a flange radially extending from said plug portion.

16. A device as claimed in claim 13, wherein said cap comprises a plug portion adapted for reversible screwable sealable engagement with respect to said inlet opening, said plug portion comprising an external screw thread adapted for sealing helical engagement with a complementary internal screw thread within said inner member.

17. A device as claimed in claim 16, wherein said cap further comprises a flange radially extending from said plug portion.

18. A device as claimed in claim 16, wherein said cap comprises a finger gripping knurled cylindrical surface.

19. A device as claimed in claim 13, wherein said cap comprises indicia marked on an external surface thereof.

20. A device as claimed in claim 19, wherein said indicia comprise the characters "+" and "−", and wherein said indicia are laterally aligned with said at least one first portal and said at least one second portal, respectively.

21. A device as claimed in claim 13, wherein said cap is made from a biocompatible material, such as polypropylene, polyethylene, or any suitable thermoplastic material.

22. A device as claimed in claim 1, wherein said inner member is made from a biocompatible material, such as polypropylene, polyethylene, or any suitable thermoplastic material.

23. A device as claimed in claim 1, wherein said external fluid environment comprises solution suitable for use as a running buffer for DNA, RNA or proteins, in particular such a solution chosen from TBE, TAE or protein running buffer solution.

24. A device as claimed in claim 1, wherein said predetermined process comprises an electroelution process.

25. A device as claimed in claim 1, wherein said at least one substance comprises a gel slice containing at least one macromolecule species of interest.

26. A device as claimed in claim 1, wherein said predetermined process comprises a dialysis process.

27. A device as claimed in claim 1, wherein said at least one substance comprises a solution of antibodies with sodium azide, and said external fluid environment comprises a suitable buffer that does not comprise sodium azide.

28. A device as claimed in claim 1, wherein said at least one substance comprises a solution of DNA with buffer of low or high pH, and said external fluid environment comprises a suitable solution having a pH of between about 7.0 and about 8.0.

29. A device as claimed in claim 1, wherein said at least one substance comprises a solution of protein with about 20% glycerol, and said external fluid environment comprises a suitable buffer that does not comprise glycerol.

30. A device for accommodating at least one substance with respect to an external fluid environment at least during a predetermined process, said device comprising an impermeable housing member defining a chamber adapted for accommodating therein said at least one substance, said housing having at least one inlet opening such as to provide opening communication between said chamber and an outside of the device, wherein said inlet opening may be sealingly closed by means of a suitable cap, said inlet opening being of a size sufficient to permit said at least one substance to be selectively inserted and removed from said chamber, said device further comprising at least one first portal and at least one second portal each separate from said at least one inlet opening, said housing further comprising semipermeable membrane means associated with said at least one first portal and said at least one second portal, said semipermeable membrane means being sealingly fixed on an outside surface of said housing such that fluid communication between said chamber and said external fluid environment via at least one first portal and at least one second portal is through said membrane means, wherein said at least one first portal and said at least one second portal are disposed in laterally opposed directions with respect to a longitudinal axis of the device, wherein said housing is substantially cylindrical having first and second longitudinally opposed ends and a substantially cylindrical sidewall, and wherein said membrane means comprises a substantially tubular sleeve having first and second longitudinal ends and made from a semipermeable membrane material, wherein said first and second longitudinal ends of the said sleeve are suitably sealing clamped onto said outside surface by suitable clamping means at least at a first and a second sealing station at each longitudinal end of said at least one first portal and said at least one second portal.

31. A device as claimed in claim 30, wherein said clamping means comprises a substantially tubular clamping member adapted for sliding over said sleeve when the same is positioned over said housing, and comprising sealing means to sealingly lock said sleeve with respect to said sealing stations, said clamping member further comprising at least one third portal and said at least one fourth portal complementary to and adapted to aligned with said at least one first portal and said at least one second portal, respectively.

32. A device as claimed in claim 31, wherein said sealing means comprises, at each said sealing station, a first circumferential rib in an inner surface of said clamping member and a second and a third circumferential ribs on the said outside surface of said housing defining a valley portion therebetween for aligning and accommodating therein said first rib when a portion of said sleeve is interposed between said first rib and said second and third ribs.

33. A device as claimed in claim 31, wherein said clamping member further comprises a foot member axially extending therefrom in a direction opposed to that of said chamber.

34. A device as claimed in claim 33, wherein said foot member comprises a plurality of flanges extending radially and longitudinally from a longitudinal axis of said housing.

35. A device as claimed in claim 33, wherein said foot member is substantially conical.

36. A device as claimed in claim 31, wherein said clamping member is made from a biocompatible material, such as polypropylene, polyethylene, or any suitable thermoplastic material.

37. A device as claimed in claim 30, wherein said sleeve is made from a biocompatible material, such as cotton linters or cellulose, cellulose acetate, polysulfone, polycarbonate, polyethylene, polyolefin, polypropylene, or polyvinylidene fluoride.

38. A device for accommodating at least one substance with respect to an external fluid environment at least during a predetermined process, said device comprising an impermeable housing member defining a chamber adapted for accommodating therein said at least one substance, said housing having at least one inlet opening such as to provide open communication between said chamber and an outside of the device, wherein said inlet opening may be sealingly closed by means of a suitable cap, said inlet opening being of a size sufficient to permit said at least one substance to be selectively inserted and removed from said chamber, said device further comprising at least one first portal and at least one second portal each separate from said at least one inlet opening, said housing further comprising semipermeable membrane means associated with said at least one first portal and said at least one second portal, said semipermeable membrane means being sealingly fixed on an outside surface of said housing such that fluid communication between said chamber and said external fluid environment via at least one first portal and at least one second portal is through said membrane means, said device further comprising a tray for mounting thereto a plurality of impermeable housing members, said tray including a base and a plurality of stands for holding said housing members.

39. A device as claimed in claim 38, wherein each stand includes a pair of facing resilient clamping members cantilevered from said base and which may be elastically spaced apart to allow a corresponding said housing member to be inserted therebetween, and to subsequently provide a clamping force on said corresponding housing member when disposed therebetween.

40. A device as claimed in claim 39, wherein said tray is made from Azetal.

41. A device as claimed in claim 39, wherein said tray further includes opposed uprights running substantially the length of said tray perpendicular to the longitudinal axis of each said housing member mounted on said tray.

42. A device as claimed in claim 39, further comprising at least one aperture in said base for facilitating the flow of water or ionic solution in a running chamber associated with said tray.

43. A device as claimed in claim 39, further comprising a plurality of trays and a suitable attachment for attaching one tray to another tray.

44. A device as claimed in claim 43, wherein said attachment includes a set of ridges on an upright of the one tray, which are adapted for aligning and intermeshing with corresponding seats disposed in a corresponding upright of the other tray.

* * * * *